United States Patent [19]
Tachikawa et al.

[11] Patent Number: 6,048,994
[45] Date of Patent: Apr. 11, 2000

[54] SELECTIVE HYDROSILYLATION METHOD USING HYDRIDO (HYDROCARBONOXY) SILANE

[75] Inventors: Mamoru Tachikawa; Kasumi Takei, both of Kanagawa, Japan

[73] Assignee: Dow Corning Asia, Ltd., Tokyo, Japan

[21] Appl. No.: 09/220,110

[22] Filed: Dec. 23, 1998

[30] Foreign Application Priority Data

Dec. 24, 1997 [JP] Japan .................................. 9-355167

[51] Int. Cl.$^7$ ...................................................... C07F 7/08
[52] U.S. Cl. ............................................. 556/479; 556/419
[58] Field of Search ..................... 556/479, 419

[56] References Cited

U.S. PATENT DOCUMENTS

| | | | |
|---|---|---|---|
| 4,599,394 | 7/1986 | Lucas ........................................ | 528/15 |
| 4,614,812 | 9/1986 | Schilling, Jr. ............................ | 556/406 |
| 4,904,732 | 2/1990 | Iwahara et al. ......................... | 525/100 |
| 5,424,470 | 6/1995 | Bank et al. .............................. | 556/479 |
| 5,449,802 | 9/1995 | Bank et al. .............................. | 556/479 |
| 5,481,016 | 1/1996 | Bank et al. .............................. | 556/479 |
| 5,486,637 | 1/1996 | Bank et al. .............................. | 556/479 |
| 5,616,763 | 4/1997 | Bank et al. .............................. | 556/479 |
| 5,756,795 | 5/1998 | Bank et al. .............................. | 556/479 |
| 5,986,124 | 11/1999 | Tachikawa et al. .................... | 556/479 |
| 5,994,573 | 11/1999 | Tachikawa et al. .................... | 556/479 |

FOREIGN PATENT DOCUMENTS

| | | | |
|---|---|---|---|
| 57-190043 | 5/1981 | Japan .............................. | C08L 71/00 |
| 63-6041 | 6/1986 | Japan .............................. | C08L 23/26 |

*Primary Examiner*—Robert Dawson
*Assistant Examiner*—Jeffrey B. Robertson
*Attorney, Agent, or Firm*—William F. Boley

[57] ABSTRACT

A method for hydrosilylating a vinyl-substituted aromatic compound comprising reacting a hydrido (hydrocarbonoxy) silane compound with the vinyl-substituted aromatic compound in the presence of a platinum or platinum compound catalyst and a carboxylic acid. The presence of the carboxylic acid increases the positional selectivity of addition in the hydrosilylation reaction and reduces the polymerization of vinyl groups even in the case of a high-temperature or long-term hydrosilylation reaction.

14 Claims, No Drawings

SELECTIVE HYDROSILYLATION METHOD USING HYDRIDO (HYDROCARBONOXY) SILANE

BACKGROUND OF INVENTION

The present invention is a method for making industrially important aromatic-substituted (hydrocarbonoxy)silane compounds which are utilized in, for example, silane coupling agents. Hydrido (hydrocarbonoxy)silane compounds, as typified by SiH-functional alkoxysilanes, are important intermediates for modified silicones, in the surface modification of various types of substrates, and as crosslinking agents in curing reactions of polymers.

Aromatic substituent groups are introduced onto hydrido (hydrocarbonoxy)silane compounds for various purposes, including improvement of heat resistance, control of refractive index, and improvement of compatibility with other organic compounds or polymers. Such compounds containing aromatic groups include phenylsilicon compounds in which aromatic rings are bonded directly to silicon atoms, as typified by phenylsilane compounds and phenylsilicon derivatives; and aralkylsilicon compounds in which aromatic rings are bonded to silicon atoms via hydrocarbon groups such as benzylsilane compounds or silicone derivatives which have 3-phenylpropyl groups or phenethyl groups. Among these compounds, phenyl groups bonded directly to silicon atoms can be manufactured by the reaction of metallic silicon with chlorobenzene (i.e., ie so-called direct method), a dehydration reaction between benzene and hydridochlorosilane by means of a boron chloride catalyst, or an equivalent organic reaction such as the Grignard method. Aralkylsilicon bonds can also be made by an equivalent organic reaction such as the Grignard method, however the making of 3-phenylpropyl groups or phenethyl groups can be accomplished more economically using a hydrosilylation reaction of aromatic compounds which have unsaturated groups, such as allylbenzene or styrene. In particular, numerous vinyl-substituted forms of aromatic compounds such as benzene, naphthalene, and pyridine and vinyl-substituted forms of derivatives of benzene, naphthalene and pyridine are known. Such compounds are commercially available and are optimal for the synthesis of silicon compounds which have various types of substituent groups. Generally, however, vinyl groups which are directly bonded to aromatic rings have readily polymerize, so that considerable portions are lost by polymerization when a hydrosilylation reaction is conducted over a long period of time or at a high temperature. In addition, a hydrosilylation reaction of vinyl groups bonded directly to aromatic rings is poor in terms of positional selectivity of the addition, so that the product is a mixture of 2-arylethylsilicon compounds and 1-arylethylsilicon compounds and the separation of these components is difficult. Furthermore in hydrosilylation reactions it is frequently necessary to add oxygen to the reaction atmosphere in order to realize and maintain catalyst activity, therefore there is a danger of ignition and explosion.

The object of the present invention is to solve the two problems involved in the abovementioned hydrosilylation reactions of vinyl-substituted aromatic compounds, that is (1) the low positional selectivity of addition and (2) the fact that high-temperature or long-term hydrosilylation reactions must be avoided in order to avoid polymerization of the vinyl groups.

The present invention is characterized by the following: in a hydrosilylation reaction using a platinum or platinum compound catalyst the positional selectivity of addition is greatly improved and the reactivity is improved at a low oxygen partial pressure or in the absence of oxygen by causing a carboxylic acid compound to be present in the reaction system when a hydrido (hydrocarbonoxy)silane compound with a low reactivity is reacted with an aromatic vinyl compound.

SUMMARY OF INVENTION

A method for hydrosilylating a vinyl-substituted aromatic compound comprising reacting a hydrido (hydrocarbonoxy) silane compound with the vinyl-substituted aromatic compound in the presence of a platinum or platinum compound catalyst and a carboxylic acid. The presence of the carboxylic acid increases the positional selectivity of addition in the hydrosilylation reaction and reduces the polymerization of vinyl groups even in the case of a high-temperature or long-term hydrosilylation reaction.

DESCRIPTION OF INVENTION

The present invention is a method for making aromatic-substituted (hydrocarbonoxy)silane compounds comprising reacting a hydrido (hydrocarbonoxy)silane compound described by formula $$HSiR_n(OR')_{3-n} \quad (1)$$

with an aromatic vinyl compound in the presence of a platinum or a platinum compound catalyst and a carboxylic acid compound; where each R is an independently selected hydrocarbon group selected from the group consisting of hydrocarbon groups comprising 1 to 10 carbon atoms and hydrocarbon groups comprising 1 to 10 carbon atoms which have at least one of the carbon atoms bonded to an atom selected from the group consisting of O, F, Cl, Br, I, and Si; each R' is an independently selected hydrocarbon group selected from the group consisting of hydrocarbon groups comprising 1 to 18 carbon atoms and hydrocarbon atoms comprising 1 to 18 carbon atoms which have a least one of the carbon atoms bonded to an atoms selected from the group consisting of O, F, Cl, Br, I, and Si; and n=0, 1, or 2.

Description of Hydrido (hydrocarbonoxy)silane Compounds

The hydrido (hydrocarbonoxy)silane compounds described by formula (1) are compounds in which hydrogen atoms are bonded to silicon atoms and in which at least one hydrocarbonoxy group is bonded to such a silicon atom. Here, the term "hydrocarbonoxy group" refers to a moiety corresponding to —OR' in formula (1), where a hydrocarbon group or a hydrocarbon group that contains prescribed atoms of O, F, Cl, Br, I, or Si is bonded to a silicon atom via an oxygen atom. Here, different hydrocarbonoxy groups may be bonded to the same silicon atom. When n=2, the two R groups may be the same or different. In cases where one or two hydrocarbonoxy groups are bonded to such a silicon atom, the remaining substituent groups bonded to the silicon atom are hydrogen atoms or hydrocarbon groups expressed by R in formula (1).

Examples of substituent R groups include alkyl groups such as methyl, ethyl, n-propyl, isopropyl, n-butyl, t-butyl, pentyl, hexyl, octyl, and decyl; alkenyl groups such as 2-propenyl, hexenyl, and octenyl; aralkyl groups such as benzyl and phenethyl; aryl groups such as phenyl, tolyl, and xylyl. Examples of substituent R groups include chloromethyl, 4-chlorophenyl, trimethylsilylmethyl, and 2-methoxyethyl, in the case of hydrocarbon groups with 1 to 10 carbon atoms which also have bonded to at least one of the carbon atoms an atom selected from the group consisting of O, F, Cl, Br, I and Si.

In the present method is preferred that each R and R" is an independently selected hydrocarbon group selected from the group consisting of hydrocarbon groups comprising 1 to 10 carbon atoms and hydrocarbon groups comprising 1 to 10 carbon atoms which have atoms selected from the group consisting of O, F, Cl, Br, I, and Si; and n=1 or 2.

Examples of R' include the same groups as those cited for the abovementioned R.

Specific examples of the hydrido (hydrocarbonoxy)silane include trialkoxysilanes, trialkenoxysilanes, and triaryloxysilanes. Examples of trialkoxysilanes include trimethoxysilane, triethoxysilane, tri-n-propoxysilane, triisopropoxysilane, tributoxysilane, triisopropenoxysilane, and triphenoxysilane. Examples of dialkoxysilanes, dialkenoxysilanes, and diaryloxysilanes include methyldimethoxysilane, methyldiethoxysilane, methyldi-n-propoxysilane, methydiisopropenoxysilane, methyldiphenoxysilane, ethyldimethoxysilane, ethyldiethoxysilane, n-propyldimethoxysilane, n-propyldiethoxysilane, 3,3,3-trifluoropropyldimethoxysilane, 3,3,3-trifluoropropyldiethoxysilane, n-hexyldimethoxysilane, n-hexyldiethoxysilane, n-octyldimethoxysilane, n-octyldiethoxysilane, benzyldimethoxysilane, benzyldiethoxysilane, phenethyldimethoxysilane, phenethyldiethoxysilane, phenyldimethoxysilane, and phenyldiethoxysilane. Examples of monoalkoxysilanes, monoalkenoxysilanes, and monoaryloxysilanes include dimethylmethoxysilane, dimethylethoxysilane, dimethyl-n-propoxysilane, dimethylisopropenoxysilane, dimethylphenoxysilane, diethylmethoxysilane, methylethylethoxysilane, n-propyl(methyl)methoxysilane, n-propyl(methyl)ethoxysilane, 3,3,3-trifluoropropyl(methyl)methoxysilane, bis (3,3,3-trifluoropropyl) ethoxysilane, n-hexyl(methyl)methoxysilane, di(n-hexyl) ethoxysilane, n-octyl (methyl)methoxysilane, di(n-octyl) ethoxysilane, benzyl(methyl)methoxysilane, phenethyl (methyl) methoxysilane, and methylphenylmethoxysilane. Examples of hydrido (hydrocarbonoxy)silanes with mixed alkoxy groups, alkenoxy groups, aralkyloxy groups, and aryloxy groups include diethoxypropenoxysilane, dimethoxyphenoxysilane, diphenoxypropenoxysilane, and methylmethoxyphenethoxysilane. Other examples of the hydrido (hydrocarbonoxy)silane include compounds in which R or R' are chloromethyl groups, 4-chlorophenyl groups, trimethylsilylmethyl groups, or 2-methoxyethyl groups.

These hydrido (hydrocarbonoxy)silane compounds are selected according to their reactivity or according to the application of the hydrido (hydrocarbonoxy)silyl-group-containing compound that is to be manufactured. Ordinarily taking reactivity into account, it is preferred that the hydrido (hydrocarbonoxy)silane compound be an alkoxysilane.

Description of Carboxylic Acid Compounds

The carboxylic acid compounds used in the present invention are compounds listed under the following (a), (b), (c), and (d):

(a) carboxylic acids, there are no particular restrictions on these carboxylic acids as long as the acids have carboxyl groups. Examples of such carboxylic acids include saturated carboxylic acids, unsaturated carboxylic acids, monocarboxylic acids, and dicarboxylic acids. The portions of these carboxylic acids other than the carboxyl groups are ordinarily selected from the group consisting of saturated or unsaturated aliphatic hydrocarbon groups, aromatic hydrocarbon groups, halogenated hydrocarbon groups, and hydrogen atoms. In addition, substituent groups such as amino groups, silyl groups, or hydroxyl groups may also be bonded to these hydrocarbon groups;

(b) carboxylic anhydrides;

(c) silylated carboxylic compounds (d) compounds which generate carboxylic acid compounds of the abovementioned (a), (b), or (c) by decomposition or reaction in the method during the hydrosilylation reaction method.

In the present method it is necessary that the carboxylic acid compound be present in the method when the hydrosilylation reaction takes place. Accordingly, it is necessary to add such a compound to the method prior to the initiation of the hydrosilylation reaction or by the early stages of the reaction.

Specific examples of carboxylic acids useful in the present method include saturated monocarboxylic acids such as formic acid, acetic acid, propionic acid, n-butyric acid, isobutyric acid, hexanoic acid, cyclohexanoic acid, lauric acid, and stearic acid; saturated dicarboxylic acids such as oxalic acid and adipic acid; aromatic carboxylic acids such as benzoic acid and para-phthalic acid; substituted carboxylic acids such as chloroacetic acid, dichloroacetic acid, trifluoroacetic acid, para-chlorobenzoic acid, and trimethylsilylacetic acid in which the hydrogen atoms of the hydrocarbon groups of the carboxylic acid are replaced by halogen atoms or organosilyl groups; unsaturated fatty acids such as acrylic acid, methacrylic acid, and oleic acid; and compounds which have hydroxy groups, carbonyl groups, or amino groups in addition to carboxyl groups, for example, hydroxy acids such as lactic acid; keto acids such as acetoacetic acid; aldehyde acids such as glyoxylic acid; and amino acids such as glutamic acid. Specific examples of silylated carboxylic acids include trialkylsilylates of carboxylic acids such as trimethylsilyl formate, trimethylsilyl acetate, triethylsilyl propionate, trimethylsilyl benzoate, and trimethylsilyl trifluoroacetate; and di-, tri- and tetracarboxylates such as dimethyldiacetoxysilane, methyltriacetoxysilane, and silicon tetrabenzoate.

Examples of carboxylic anhydrides which can be used in the present method include acetic anhydride, propionic anhydride, and benzoic anhydride. Examples of compounds which can generate the carboxylic acid compounds by decomposition or reactions in the present method include carboxylic acid halides such as acetyl chloride, butyryl chloride, and benzoyl chloride and metal salts of carboxylic acids.

The carboxylic acid compounds are preferably selected from the group consisting of carboxylic acids, silylated carboxylic acids, and carboxylic anhydrides.

These carboxylic acid compounds can be effectively used by being added to the present method in an amount of of 0.001 Wt. % to 20 Wt. %; however, in order to achieve a sufficient effect and also use the compounds efficiently, it is desirable that such compounds be added in an amount of 0.01 Wt. % to 20 Wt. % and preferably 0.01 Wt. % to 5 Wt. %. Here, the amount of the carboxylic acid compound added refers to its weight as a weight percent of the mixture comprising the hydrido (hydrocarbonoxy)silane compound, aromatic vinyl compound, platinum or platinum compound catalyst, and the carboxylic acid compound.

Description of Aromatic Vinyl Compound

The term "aromatic vinyl compound" as used in the present methods refers to either (a) an aromatic compound with a structure in which vinyl groups are bonded directly to an aromatic rings or (b) a derivative of an aromatic compound in which a vinyl group is bonded directly to an aromatic ring. There are no particular restrictions on these compounds, as long as the compounds have sufficient reactivity to achieve the effect of the present invention. For example, polymers which have aromatic rings to which vinyl groups are bonded are also included. Furthermore, the abovementioned compounds listed under (a) and (b) may also contain atoms other than carbon and hydrogen atoms; examples of such atoms include O, N, F, Cl, Br, I, S, and Si.

In cases where such aromatic vinyl compounds have an aromatic-substituted amine structure, aromatic-substituted primary amines or aromatic-substituted secondary amines are candidates for use.

Specific examples of such aromatic vinyl compounds include styrene, styrene derivatives such as 4-vinylpheny, para-chlorostyrene, para-methylstyrene, para-methoxystyrene, para-trimethylstyrene, meta-chlorostyrene, para-bromostyrene, (chloromethyl)styrene, and divinylbenzene; polycyclic aromatic vinyl derivatives such as vinylnaphthalene and vinylanthracene; non-benzenoid aromatic vinyl compounds such as vinylfuran, vinylthiophene, vinylpyrrole, and vinylpyridine; and vinylmetallocene compounds such as vinylferrocene and vinylcyclopentadienyl manganese tricarbonyl.

In the present method it is preferred that the aromatic vinyl compound be selected from the group consisting of styrene, styrene derivatives, and polycyclic aromatic vinyl derivatives.

Description of Platinum or Platinum Compound Catalyst

In the present method, the platinum or platinum compound catalyst may be selected from the group consisting of platinum metal and platinum compounds where the platinum has a minus charge or is 0-valent, divalent, or tetravalent, and platinum colloids. Specific examples of compounds with a minus charge include platinum carbonyl cluster anion compounds such as $(Pt_3(CO)_6)^{2-}$, $(Pt_3(CO)_6)_2^{2-}$ and $(Pt_3(CO)_6)_4^{2-}$. Examples of 0-valent platinum compounds include platinum (0) divinyltetramethyldisiloxane complexes, platinum (0) tetravinyltetramethylcyclotetrasiloxane complexes, platinum (0) ethylene complexes, and platinum (0) styrene complexes. Examples of divalent platinum compounds include $Pt(II)Cl_2$, $Pt(II)Br_2$, bis (ethylene)$Pt(II)Cl_2$, (1,5-cyclooctadiene) $Pt(II)Cl_2$, platinum (II) acetylacetonate, and bis (benzonitrile)$Pt(II)Cl_2$. Examples of tetravalent platinum compounds include $Pt(IV)Cl_4$, $H_2Pt(IV)Cl_6$, $Na_2Pt(IV)Cl_6$, and $K_2Pt(IV)Cl_6$. Among these compounds, platinum (0) divinyltetramethyldisiloxane complexes and alcohol solutions of chloroplatinic acid may be cited as examples of especially desirable platinum compounds from the standpoint of utility such as solubility in organic solvents and stability of the catalyst solution. The amount of platinum required for the hydrosilylation reaction of a given amount of substrate varies according to factors such as the type of substrate, reaction temperature, and reaction time. Generally, such a catalyst can be used in the range of $10^{-3}$ moles to $10^{-8}$ moles of platinum per mole of hydrido (hydrocarbonoxy)silane compound. From the standpoints of catalyst economy and reaction time, use in the range of $10^{-4}$ moles to $10^{-7}$ moles of platinum is preferred, on the same basis.

The temperature at which the reaction of the present method is effected may be about 0° C. to 300° C.; however a temperature of about 30° C. to 250° C. is preferred from the standpoints of achieving a suitable reaction rate and the stability of the product and the substrates participating in the reaction.

In the present method, the use of a solvent is optional. If desired, hydrocarbon solvents, oxygen-containing organic solvents or silicones, for example, may be used as solvents for the catalyst component, to dissolve the substrates, or to control the temperature of the method. Examples of solvents which are suitable for such purposes include saturated or unsaturated hydrocarbon compounds such as hexane, cyclohexane, heptane, octane, dodecane, benzene, toluene, xylene, and dodecylbenzene; halogenated hydrocarbon compounds such as chloroform, methylene chloride, chlorobenzene, and ortho-dichlorobenzene; ethers, esters, and silicones such as polydimethylsiloxanes with trimethylsilyl groups on both terminals and hexamethyldisiloxane.

The aromatic-substituted (hydrocarbonoxy)silane compounds produced by the present method are compounds in which at least one hydrocarbonoxy group is bonded to a silicon atom and which have at least one aromatic hydrocarbon group. In cases where substituent groups other than these are present, hydrocarbon groups defined by R in formula (1) are bonded.

A preferred embodiment of the present method is that in which the aromatic vinyl compounds are (a) compounds selected from the group consisting of styrene, styrene derivatives, and polycyclic aromatic vinyl derivatives, or (b) compounds selected from the group consisting of styrene, styrene derivatives, and polycyclic aromatic vinyl derivatives which have one or more atoms selected from the group consisting of O, N, F, Cl, Br, I, S, and Si with the proviso that in cases where the compound used has an aromatic-substituted amine structure the candidate compounds are restricted to aromatic-substituted primary amines or aromatic-substituted secondary amines, and which in the hydrido (hydrocarbonoxy)silane compound each R and R' are independently selected hydrocarbon groups selected from the group consisting of hydrocarbon groups comprising 1 to 10 carbon atoms and hydrocarbon atoms comprising 1 to 10 atoms which have at least one of the carbon atoms bonded to an atom selected from the group consisting of O, F, Cl, Br, I, and Si; and n=1 or 2.

The present method is described in detail in terms of the following working examples. There examples are not intended to limit the scope of the claims herein.

In the characterization of products in the examples, GC-MS indicates gas chromatography-mass spectroscopy analysis. The conversion rate indicates the amount of the aromatic vinyl compound reacted and the yield indicates the amount of product produced relative to the amount of aromatic vinyl compound reacted.

The (hydrocarbonoxy)silane compounds, alkylsilane compounds, and siloxane compounds used in the present working examples were either commercially purchased compounds or compounds synthesized by standard known methods. The unsaturated compounds were commercially purchased compounds used "as is".

WORKING EXAMPLE 1

Reaction of Styrene and Triethoxysilane by Means of a Platinum Catalyst in the Presence of Acetic Acid 208 mg Of styrene, 328 mg of triethoxysilane, and 52 mg of toluene were placed in a glass reaction tube and 0.004 ml of acetic acid was added. Then, 0.002 ml of a toluene solution of a 0-valent platinum complex of divinyltetramethyldisiloxane (platinum content: 0.4 Wt. %) was added to this mixture. The reaction tube was sealed with Teflon tape and heated for 1 hour in an oil bath at 50° C. When the tube contents were analyzed by GC-MS following cooling, the conversion rate of styrene was 89.4% and phenethyltriethoxysilane was produced at a yield of 84.7%. The yield of α-(methylbenzyl)triethoxysilane was 0.7%.

COMPARATIVE EXAMPLE 1

Reaction Of Styrene And Triethoxysilane By Means Of A Platinum Catalyst Without The Addition Of A Carboxylic Acid Compound 208 mg Of styrene, 328 mg of triethoxysilane, and 52 mg of toluene were placed in a glass reaction tube. Next, 0.002 ml of a toluene solution of a 0-valent platinum complex of divinyltetramethyldisiloxane (platinum content: 0.4 Wt. %) was added to this mixture. The reaction tube was sealed with a Teflon tape and heated for 1 hour in an oil bath at 50° C. When the tube contents were analyzed by GC-MS following cooling, the conversion rate of styrene was 7.4% and phenethyltriethoxysilane was produced at a yield of 1.6%. The yield of (α-methylbenzyl) triethoxysilane was 0.9%

WORKING EXAMPLE 2

Reaction of Chloromethylstyrene and Methyldimethoxysilane by Means of a Platinum Catalyst in the Presence of Formic Acid 305 mg Of chloromethylstyrene and 255 mg of methyldimethoxysilane were placed in a glass reaction tube and 0.001 ml of formic acid was added. Then, 0.0045 ml of a toluene solution of a 0-valent platinum complex of divinyltetramethyldisiloxane (platinum content: 0.04 Wt. %) was added to this mixture. The reaction tube was sealed with Teflon tape and heated for 30 minutes in an oil bath at 50° C. When the tube contents were analyzed by GC-MS following cooling, the conversion rate of chloromethylstyrene was 28% and β-(chloromethylphenyl) ethyltriethoxysilane was produced at a yield of 25%. The yield of α-(chloromethylphenyl)ethyltriethoxysilane was 2.2%.

COMPARATIVE EXAMPLE 2

The Same Reaction as that Performed in Working Example 2 was Performed Without Adding a Carboxylic Acid The conversion rate of chloromethylstyrene was 8.8% and β-(chloromethylphenyl) ethyltriethoxysilane was produced at a yield of 3.7%. The yield of α-(chloromethylphenyl) ethyltriethoxysilane was 5.1%.

WORKING EXAMPLE 3

Reaction of Styrene and Triethoxysilane by Means of a Platinum Catalyst in the Presence of Trifluoroacetic Acid 208 mg Of styrene, 328 mg of triethoxysilane, and 52 mg of toluene were placed in a glass reaction tube and 0.005 ml of trifluoroacetic acid was added. Then, 0.002 ml of a toluene solution of a 0-valent platinum complex of divinyltetramethyldisiloxane (platinum content: 0.4 Wt. %) was added to this mixture. The reaction tube was sealed with Teflon tape and heated for 1 hour in an oil bath at 50° C. When the tube contents were analyzed by GC-MS following cooling, the conversion rate of styrene was 41.4% and phenethyltriethoxysilane was produced at a yield of 30.5%. The yield of (α-methylbenzyl)triethoxysilane was 1.2%.

WORKING EXAMPLE 4

Reaction of 4-Vinylbiphenyl and Triethoxysilane by Means of a Platinum Catalyst in the Presence of Cyclohexanoic Acid 361 mg Of 4-vinylbiphenyl and 394 mg of triethoxysilane were placed in a glass reaction tube and 0.0009 ml of cyclohexanoic acid was added. Then, 0.009 ml of a toluene solution of a 0-valent platinum complex of divinyltetramethyldisiloxane (platinum content: 0.0044 Wt. %) was added to this mixture. The reaction tube was sealed with Teflon tape and heated for 30 minutes in an oil bath at 50° C. When the tube contents were analyzed by GC-MS following cooling, the conversion rate of 4-vinylbiphenyl was 36% and para-phenylphenethyltriethoxysilane was produced at a yield of 32%. The yield of α-(4-biphenylyl) triethoxysilane was 3%.

COMPARATIVE EXAMPLE 3

The Same Reaction as that Performed in Working Example 2 was Performed Without Adding a Carboxylic Acid The conversion rate of 4-vinylbiphenyl was 18% and para-phenylphenethyltriethoxysilane was produced at a yield of 14%. The yield of α-(4-biphenylyl) triethoxysilane was 3.8%.

WORKING EXAMPLE 5

Reaction of Styrene and Dimethylethoxysilane by Means of a Platinum Catalyst in the Presence of acetic Acid 312 mg Of styrene and 312 mg of dimethylethoxysilane were placed in a glass reaction tube and 0.006 ml of acetic acid was added. Then, 0.001 ml of a toluene solution of a 0-valent platinum complex of divinyltetramethyldisiloxane (platinum content: 0.4 Wt. %) was added to this mixture. The reaction tube was sealed with Teflon tape and heated for 30 minutes in an oil bath at 41° C. When the tube contents were analyzed by GC-MS following cooling, the conversion rate of styrene was 80% and phenethyldimethylethoxysilane was produced at a yield of 74.5%. The yield of (α-methylbenzyl) dimethylethoxysilane was 5.5%

COMPARATIVE EXAMPLE 4

Reaction of Styrene and Dimethylethoxysilane by Means of a Platinum Catalyst Without Adding a Carboxylic Acid The same reaction as that performed in Working Example 5 was performed without adding a carboxylic acid. When the reaction product was analyzed by GC-MS, the conversion rate of styrene was 36% and phenethyldimethylethoxysilane was produced at a yield of 27%. The yield of (α-methylbenzyl) dimethylethoxysilane was 8.5%.

WORKING EXAMPLE 6

Reaction of Styrene and Triethoxysilane by Means of a Platinum Catalyst in the Presence of Methyltriacetoxysilane 130 mg Of styrene and 217 mg of triethoxysilane were placed in a glass reaction tube and 0.0032 mg of methyltriacetoxysilane was added. Next, 0.0045 ml of a toluene solution of a 0-valent platinum complex of divinyltetramethyldisiloxane (platinum content: 0.04 Wt. %) was added to this mixture. The reaction tube was sealed with Teflon tape and heated for 30 minutes in an oil bath at 50° C. When the tube contents were analyzed by GC-MS following cooling, the conversion rate of styrene was 98% and phenethyltriethoxysilane was produced at a yield of 96%. The yield of (α-methylbenzyl) triethoxysilane was 0.7%.

WORKING EXAMPLE 7

Reaction of Styrene and Triethoxysilane by Means of a Platinum Catalyst in the Presence of acetic Anhydride 130 mg Of styrene and 217 mg of triethoxysilane were placed in a glass reaction tube and 0.0015 ml of acetic anhydride was added. Next, 0.0045 ml of a toluene solution of a 0-valent platinum complex of divinyltetramethyldisiloxane (platinum content: 0.04 Wt. %) was added to this mixture. The reaction tube was sealed with Teflon tape and heated for 30 minutes in an oil bath at 50° C. When the tube contents were analyzed by GC-MS following cooling, the conversion rate of styrene was 16% and phenethyltriethoxysilane was produced at a yield of 13%. The yield of (α-methylbenzyl) triethoxysilane was 2%.

WORKING EXAMPLE 8

Reaction of Styrene and Triethoxysilane by Means of a Platinum Chloride Catalyst in the Presence of Lauric Acid 130 mg Of styrene and 217 mg of triethoxysilane were placed in a glass reaction tube and 0.0014 mg of lauric acid was added. Next, 0.01 ml of an isopropyl alcohol solution of chloroplatinic acid (platinum content: 0.02 Wt. %) was added to this mixture. The reaction tube was sealed with Teflon tape and heated for 30 minutes in an oil bath at 50° C. When the tube contents were analyzed by GC-MS following cooling, the conversion rate of styrene was 35% and phenethyltriethoxysilane was produced at a yield of 23%. The yield of (α-methylbenzyl)triethoxysilane was 0.4%.

COMPARATIVE EXAMPLE 5

Reaction of Styrene and Triethoxysilane by Means of a Platinum Chloride Catalyst Without the Addition of a Carboxylic Acid 130 mg Of styrene and 217 mg of triethoxysilane were placed in a glass reaction tube and 0.01 ml of an isopropyl alcohol solution of chloroplatinic acid (platinum content: 0.02 Wt. %) was added to this mixture. The reaction tube was sealed with Teflon tape and heated for 30 minutes in an oil bath at 50° C. When the tube contents were analyzed by GC-MS following cooling, the conversion rate of styrene was 3% and phenethyltriethoxysilane was produced at a yield of 1.5%. The yield of (α-methylbenzyl) triethoxysilane was 0.5%.

WORKING EXAMPLE 9

Reaction of 4-Chlorostyrene and Methyldiethoxysilane By Means of a Platinum Catalyst in the Presence of acetic Acid 440 mg Of 4-chlorostyrene and 510 mg of methyldiethoxysilane were placed in a glass reaction tube and 0.005 ml of acetic acid was added. Then, 0.007 ml of a toluene solution of a 0-valent platinum complex of divinyltetramethyldisiloxane (platinum content: 0.2 Wt. %) was added to this mixture. The reaction tube was sealed with Teflon tape and heated for 1 hour in an oil bath at 50° C. When the tube contents were analyzed by GC-MS following cooling, the conversion rate of 4-chlorostyrene was 81% and β-(4-chlorophenethyl) methyldiethoxysilane was produced at a yield of 49%. The yield of α-(4-chlorophenyl) ethylmethyldiethoxysilane was 2.2%.

COMPARATIVE EXAMPLE 6

Reaction of 4-Chlorostyrene and Methyldiethoxysilane By Means of a Platinum Catalyst Without the Addition of a Carboxylic Acid 440 mg Of 4-chlorostyrene and 510 mg of methyldiethoxysilane were placed in a glass reaction tube. Then, 0.007 ml of a toluene solution of a 0-valent platinum complex of divinyltetramethyldisiloxane (platinum content: 0.2 Wt. %) was added to this mixture. The reaction tube was sealed with Teflon tape and heated for 1 hour in an oil bath at 50° C. When the tube contents were analyzed by GC-MS following cooling, the conversion rate of 4-chlorostyrene was 46% and β-(4-chlorophenethyl) methyldiethoxysilane was produced at a yield of 17%. The yield of α-(4-chlorophenyl) ethylmethyldiethoxysilane was 17%.

WORKING EXAMPLE 10

Reaction of Divinylbenzene and Triethoxysilane by Means of a Platinum Catalyst in the Presence of acetic Acid 871 mg Of divinylbenzene and 4.35 g of triethoxysilane were placed in a glass reaction tube and 0.005 ml of acetic acid was added. Next, 0.015 ml of a toluene solution of a 0-valent platinum complex of divinyltetramethyldisiloxane (platinum content: 0.2 Wt. %) was added to this mixture. The reaction tube was sealed with a Teflon tape and heated for 30 minutes in an oil bath at 50° C. When the tube contents were analyzed by gas chromatography following cooling, the conversion rate of divinylbenzene was 99%; bis (2-triethoxysilylethyl) benzene was produced at a yield of 97%, (1-triethoxysilylethyl) (2-triethoxysilylethyl) benzene was produced at a yield of 1.6%, and (triethoxysilyl) ethylstyrene was produced at a yield of 0.1%. No production of bis (1-triethoxysilylethyl)benzene was observed.

COMPARATIVE EXAMPLE 7

Reaction of Divinylbenzene and Triethoxysilane by Means of a Platinum Catalyst Without Acetic Acid 871 mg Of divinylbenzene and 4.35 g of triethoxysilane were placed in a glass reaction tube and 0.015 ml of a toluene solution of a 0-valent platinum complex of divinyltetramethyldisiloxane (platinum content: 0.2 Wt. %) was added to this mixture. The reaction tube was sealed with Teflon tape and heated for 30 minutes in an oil bath at 50° C. When the tube contents were analyzed by GC-MS following cooling, the conversion rate of divinylbenzene was 56%; bis (2-triethoxysilylethyl) benzene was produced at a yield of 2.8%, (1-triethoxysilylethyl) (2-triethoxysilylethyl) benzene was produced at a yield of 3.7%, and bis (1-triethoxysilylethyl) benzene was produced at a yield of 0.1%. No production of (triethoxysilyl) ethylstyrene was observed.

WORKING EXAMPLE 11

Reaction of 4-Dimethylsilylstyrene and Methyldimethoxysilane by Means of a Platinum Catalyst in the Presence of acetic Acid 325 mg Of 4-imethylsilylstyrene, 212 mg of methyldimethoxysilane, and 83 mg of toluene were placed in a glass reaction vessel and 0.005 ml of acetic acid was added. Next, 0.001 ml of an isopropyl alcohol solution of chloroplatinic acid (platinum content: 0.39 Wt. %) was added to this mixture. The reaction tube was sealed with Teflon tape and heated for 0.5 hours in an oil bath at 50° C. When the contents were analyzed by GC-MS following cooling, the conversion rate of 4-dimethylsilylstyrene was 63.6% and (4-(dimethylsilyl) phenethyl) methyldimethoxysilane was produced at a yield of 4.9%. The yield of α-(4-(dimethylsilyl)phenyl)ethyl) methyldimethoxysilane was 1.8%.

COMPARATIVE EXAMPLE 8

Reaction of 4-Dimethylsilylstyrene and Methyldimethoxysilane by Means of a Platinum Catalyst Without the Addition of a Carboxylic Acid Compound 325 mg Of 4-dimethylsilylstyrene, 212 mg of methyldimethoxysilane, and 83 mg of toluene were placed in a glass reaction vessel and 0.001 ml of an isopropyl alcohol solution of chloroplatinic acid (platinum content: 0.39 Wt. %) was added to this mixture. The reaction tube was sealed with Teflon tape and heated for 0.5 hours in an oil bath at 50° C. When the tube contents were analyzed by GC-MS following cooling, the conversion rate of 4-dimethylsilylstyrene was 12.7% and (4-(dimethylsilyl)phenethyl)methyldimethoxysilane was produced at a yield of 4.1%. The yield of (α-(4-(dimethylsilyl)phenyl)ethyl) methyldimethoxysilane was 3.3%.

COMPARATIVE EXAMPLE 9

Reaction of Styrene and Triethylsilane by Means of a Platinum Catalyst in the Presence of acetic Acid 265 mg Of styrene and 295 mg of triethylsilane were placed in a glass reaction tube and 0.002 ml of acetic acid was added. Next, 0.002 ml of a toluene solution of a 0-valent platinum complex of divinyltetramethyldisiloxane (platinum content: 0.4 Wt. %) was added to this mixture. The reaction tube was sealed with Teflon tape and heated for 1.5 hours in an oil bath at 41° C. When the tube contents were analyzed by GC-MS following cooling, the conversion rate of styrene was 2%; no phenethyltriethoxysilane or (α-methylbenzyl) triethoxysilane could be detected.

WORKING EXAMPLE 12

Reaction of Styrene and Triethoxysilane by Means of a Platinum Catalyst in the Presence of an Unsaturated Carboxylic Acid 200 mg of styrene, 320 mg of triethoxysilane, and 370 mg of toluene were placed in a glass reaction tube and 0.0014 ml of methacrylic acid was added. Next, 0.002 ml of a toluene solution of a 0-valent platinum complex of divinyltetramethyldisiloxane (platinum content: 0.4 Wt. %) was added to this mixture. The reaction tube was sealed with Teflon tape and heated for 30 minutes in an oil bath at 50° C. When the tube contents were analyzed by GC-MS following cooling, the conversion rate of styrene was 66.3%, phenethyltriethoxysilane was produced at a yield of 64.7%, and the yield of (α-methylbenzyl)triethoxysilane was 1.0%.

COMPARATIVE EXAMPLE 10

Reaction of Styrene and Triethoxysilane by Means of a Platinum Catalyst in the Presence of a Carboxylic Acid Ester 200 mg Of styrene, 320 mg of triethoxysilane, and 370 mg of toluene were placed in a glass reaction tube and 0.004 ml of ethyl acetate was added. Next, 0.01 ml of a toluene solution of a 0-valent platinum complex of divinyltetramethyldisiloxane (platinum content: 0.4 Wt. %) was added to this mixture. The reaction tube was sealed with Teflon tape and heated for 30 minutes in an oil bath at 41° C. When the tube contents were analyzed by GC-MS following cooling, the conversion rate of styrene was 13.5%, phenethyltriethoxysilane was produced at a yield of 8.5%, and the yield of (α-methylbenzyl) triethoxysilane was 13.6%.

WORKING EXAMPLE 13

Reaction of 2-Vinylnaphthalene and Triethoxysilane By Means of a Platinum Catalyst in the Presence of acetic Acid 80 mg Of vinylnaphthalene, 100 mg of triethoxysilane, and 320 mg of toluene were placed in a glass reaction tube and 0.002 ml of acetic acid was added. Next, 0.020 ml of a toluene solution of a 0-valent platinum complex of divinyltetramethyldisiloxane (platinum content: 0.2 Wt. %) was added to this mixture. The reaction tube was sealed with Teflon tape and heated for 30 minutes in an oil bath at 80° C. When the tube contents were analyzed by GC-MS following cooling, the conversion rate of 2-vinylnaphthalene was 74% and 2-(2-naphthylethyl) triethoxysilane was produced at a yield of 42%. The yield of 1-(2-naphthylethyl) triethoxysilane was 0.4%.

COMPARATIVE EXAMPLE 11

Reaction of Vinylnaphthalene and Triethoxysilane By Means of a Platinum Catalyst Without the Addition of a Carboxylic Acid Compound The same reaction as that performed in Working Example 13 was performed without adding a carboxylic acid. When the reaction product was analyzed by GC-MS, the conversion rate of 2-vinylnaphthalene was 38% and 2-(2-naphthylethyl)triethoxysilane was produced at a yield of 6.4%. The yield of 1-(2-naphthylethyl)triethoxysilane was 4.0%.

We claim:

1. A method for making an aromatic-substituted (hydrocarbonoxy)silane compound comprising reacting a hydrido (hydrocarbonoxy)silane compound described by formula $HSiR_n(OR')_{3-n}$

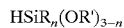

with an aromatic vinyl compound in the presence of platinum or a platinum compound catalyst and a carboxylic acid compound; where each R is an independently selected hydrocarbon group selected from the group consisting of hydrocarbon groups comprising 1 to 10 carbon atoms and hydrocarbon groups comprising 1 to 10 carbon atoms which have at least one of the carbon atoms bonded to an atom selected from the group consisting of O, F, Cl, Br, I, and Si;

each R' is an independently selected hydrocarbon group selected from the group consisting of hydrocarbon groups comprising 1 to 18 carbon atoms and hydrocarbon atoms comprising 1 to 18 carbon atoms which have at least one of the carbon atoms bonded to an atom selected from the group consisting of O, F, Cl, Br, I, and Si; and n=0, 1, or 2.

2. A method according to claim 1, where the hydrido (hydrocarbonoxy)silane compound is an alkoxysilane.

3. A method according to claim 1, where each R and R' is an independently selected hydrocarbon group selected from the group consisting of hydrocarbon groups comprising 1 to 10 carbon atoms and hydrocarbon groups comprising 1 to 10 carbon atoms having at least one of the carbon atoms bonded to an atom selected from the group consisting of O, F, Cl, Br, I, and Si.

4. A method according to claim 1, where the carboxylic acid compound is selected from a group consisting of carboxylic acids, carboxylic anhydrides, and silylated carboxylic compounds.

5. A method according to claim 1, where the carboxylic acid compound is added in an amount of 0.001 Wt. % to 20 Wt. % of the total weight of components present in the method.

6. A method according to claim 1, where the carboxylic acid compound is added in an amount of 0.01 Wt. % to 20 Wt. % of the total weight of components present in the method.

7. A method according to claim 1, where the carboxylic acid compound is added in an amount of 0.01 Wt. % to 5 Wt. % of the total weight of components present in the method.

8. A method according to claim 1, where the aromatic vinyl compound comprises atoms other than carbon and hydrogen selected from the group consisting of O, N, Cl, Br, I, S, and Si.

9. A method according to claim 1, where the aromatic vinyl compound is selected from the group consisting of styrene, styrene derivatives, and polycyclic aromatic vinyl derivatives.

10. A method according to claim 1, where the platinum or platinum compound catalyst is selected from the group consisting of platinum (0) divinyltetramethyldisiloxane complex and alcoholic solutions of chloroplatinic acid.

11. A method according to claim 1, where the reaction is effected at a temperature of about 30° C. to 250° C.

12. A method according to claim 1, where the aromatic vinyl compound is selected from the group consisting of styrene, styrene derivatives, and polycyclic aromatic vinyl derivatives which may further comprise O, N, F, Cl, Br, I, S, and Si substitutions with the proviso that if the aromatic vinyl compound is substituted with N the compounds are restricted to aromatic-substituted primary amines and aromatic-substituted secondary amines; the hydrido (hydrocarbonoxy)silane compound are those where each R and R' are independently selected hydrocarbon groups selected from the group consisting of hydrocarbon groups comprising 1 to 10 carbon atoms and hydrocarbon groups comprising 1 to 10 carbon atoms in which at least one of the carbon atoms is bonded to an atom selected from the group consisting of O, F, Cl, Br, I, and Si; and n=1 or 2.

13. A method according to claim 1, where the hydrido (hydrocarbonoxy)silane is an alkoxysilane, the aromatic vinyl compound is selected from the group consisting of styrene, styrene derivatives, and polycyclic aromatic vinyl derivatives, and the carboxylic acid compound is selected from the group consisting of carboxylic acids, carboxylic anhydrides, and silylated carboxylic compounds.

14. A method according to claim 13, where n=1 or 2.

* * * * *